US010117655B2

(12) United States Patent
Scirica et al.

(10) Patent No.: US 10,117,655 B2
(45) Date of Patent: Nov. 6, 2018

(54) LOADING UNIT LOCKING BAND FOR SURGICAL STAPLING INSTRUMENT

(71) Applicant: Covidien LP, Mansfield, MA (US)

(72) Inventors: Paul Scirica, Huntington, CT (US); Justin Williams, Southbury, CT (US); Patrick Mozdzierz, Glastonbury, CT (US); Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 457 days.

(21) Appl. No.: 14/805,547

(22) Filed: Jul. 22, 2015

(65) Prior Publication Data

US 2017/0020526 A1    Jan. 26, 2017

(51) Int. Cl.
*A61B 17/04* (2006.01)
*A61B 17/10* (2006.01)
*A61B 17/068* (2006.01)
*A61B 17/115* (2006.01)
*A61B 17/00* (2006.01)

(52) U.S. Cl.
CPC .......... *A61B 17/105* (2013.01); *A61B 17/068* (2013.01); *A61B 17/1155* (2013.01); *A61B 2017/00473* (2013.01); *A61B 2017/00477* (2013.01)

(58) Field of Classification Search
CPC . A61B 17/105; A61B 17/068; A61B 17/1155; A61B 2017/00477
USPC ........................................... 227/175.1–182.1
See application file for complete search history.

(56) References Cited

U.S. PATENT DOCUMENTS

| 2,110,397 A | * | 3/1938 | Kangas | ................. E21B 17/046 |
| | | | | 279/76 |
| 2,304,038 A | * | 12/1942 | Thompson | .......... B25B 23/0035 |
| | | | | 279/79 |
| 3,193,165 A | | 7/1965 | Akhalaya et al. | |
| 3,245,703 A | * | 4/1966 | Manly | ................. F16L 37/0847 |
| | | | | 285/319 |

(Continued)

FOREIGN PATENT DOCUMENTS

| CA | 908529 A | 8/1972 |
| CN | 201481477 U | 5/2010 |

(Continued)

OTHER PUBLICATIONS

European Search Report dated May 23, 2017, issued in EP Application No. 16189648.

(Continued)

*Primary Examiner* — Robert Long

(57) ABSTRACT

A loading unit includes a shell assembly and a locking band. The shell assembly has a proximally extending annular body. The annular body defines two hook openings that oppose one another, a lug opening positioned between the hook openings, and a central passage for receiving a portion of a surgical instrument. The locking band has an arced body with two ends, a retention hook positioned adjacent each end of the body and extending from the inner surface of the body. Each of the retention hooks is disposed within a respective one of the hook opening to retain a respective one of the ends of the locking band to the annular body. The lug is disposable through the lug opening into the central passage to secure the loading unit to a surgical instrument.

19 Claims, 11 Drawing Sheets

(56) References Cited

U.S. PATENT DOCUMENTS

| | | | |
|---|---|---|---|
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,647,241 A * | 3/1987 | Weber | F16B 7/0426 403/18 |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,869,534 A * | 9/1989 | Ketcham | F16L 37/144 285/24 |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,215,336 A * | 6/1993 | Worthing | F16L 19/005 285/319 |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,275,443 A * | 1/1994 | Klinger | F16L 37/144 285/305 |
| 5,282,810 A | 2/1994 | Allen et al. | |
| 5,285,944 A | 2/1994 | Green et al. | |
| 5,285,945 A | 2/1994 | Brinkerhoff et al. | |
| 5,291,910 A * | 3/1994 | Bui | A61H 3/02 135/68 |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,405,175 A * | 4/1995 | Bonnah, II | F02M 55/004 24/DIG. 53 |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,593,187 A * | 1/1997 | Okuda | F16L 37/088 285/305 |
| 5,609,285 A | 3/1997 | Grant et al. | |
| 5,617,601 A * | 4/1997 | McDougall | A46B 13/008 15/22.1 |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,709,674 A * | 1/1998 | Steer | A61F 5/448 604/332 |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,755,259 A * | 5/1998 | Schulze | F16K 17/30 137/460 |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |

(56) References Cited

U.S. PATENT DOCUMENTS

| | | | |
|---|---|---|---|
| D425,784 S * | 5/2000 | Beugelsdyk | D8/395 |
| 6,056,070 A * | 5/2000 | Shinohara | B25D 9/145 |
| | | | 173/128 |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,254,305 B1 * | 7/2001 | Taylor | B25G 1/04 |
| | | | 15/144.4 |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicola | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,539,920 B1 * | 4/2003 | Spiers | F02M 55/004 |
| | | | 123/456 |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,612,622 B2 * | 9/2003 | Andre | F16L 33/00 |
| | | | 285/305 |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,698,643 B2 | 3/2004 | Whitman | |
| 6,716,222 B2 | 4/2004 | McAlister et al. | |
| 6,716,233 B1 | 4/2004 | Whitman | |
| 6,726,697 B2 | 4/2004 | Nicholas et al. | |
| 6,736,031 B1 * | 5/2004 | Kang | B25B 7/12 |
| | | | 81/322 |
| 6,742,692 B2 | 6/2004 | Hartwick | |
| 6,743,244 B2 | 6/2004 | Blatter et al. | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,821,282 B2 | 11/2004 | Perry et al. | |
| 6,827,246 B2 | 12/2004 | Sullivan et al. | |
| 6,840,423 B2 | 1/2005 | Adams et al. | |
| 6,843,403 B2 | 1/2005 | Whitman | |
| 6,846,308 B2 | 1/2005 | Whitman et al. | |
| 6,852,122 B2 | 2/2005 | Rush | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,938,814 B2 | 9/2005 | Sharma et al. | |
| 6,942,675 B1 | 9/2005 | Vargas | |
| 6,945,444 B2 | 9/2005 | Gresham et al. | |
| 6,953,138 B1 | 10/2005 | Dworak et al. | |
| 6,957,758 B2 | 10/2005 | Aranyi | |
| 6,959,851 B2 | 11/2005 | Heinrich | |
| 6,978,922 B2 | 12/2005 | Bilotti et al. | |
| 6,981,941 B2 | 1/2006 | Whitman et al. | |
| 6,981,979 B2 | 1/2006 | Nicolo | |
| 6,983,958 B2 * | 1/2006 | Rautureau | F16L 37/088 |
| | | | 285/305 |
| 7,032,798 B2 | 4/2006 | Whitman et al. | |
| 7,059,331 B2 | 6/2006 | Adams et al. | |
| 7,059,510 B2 | 6/2006 | Orban, III | |
| 7,077,856 B2 | 7/2006 | Whitman | |
| 7,080,769 B2 | 7/2006 | Vresh et al. | |
| 7,086,267 B2 | 8/2006 | Dworak et al. | |
| 7,114,642 B2 | 10/2006 | Whitman | |
| 7,118,528 B1 | 10/2006 | Piskun | |
| 7,122,044 B2 | 10/2006 | Bolduc et al. | |
| 7,128,748 B2 | 10/2006 | Mooradian et al. | |
| 7,141,055 B2 | 11/2006 | Abrams et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,195,142 B2 | 3/2007 | Orban, III | |
| 7,207,168 B2 | 4/2007 | Doepker et al. | |
| 7,220,237 B2 | 5/2007 | Gannoe et al. | |
| 7,234,624 B2 | 6/2007 | Gresham et al. | |
| 7,235,089 B1 | 6/2007 | McGuckin, Jr. | |
| RE39,841 E | 9/2007 | Bilotti et al. | |
| 7,285,125 B2 | 10/2007 | Viola | |
| 7,303,106 B2 | 12/2007 | Milliman et al. | |
| 7,303,107 B2 | 12/2007 | Milliman et al. | |
| 7,309,341 B2 | 12/2007 | Ortiz et al. | |
| 7,322,994 B2 | 1/2008 | Nicholas et al. | |
| 7,325,713 B2 | 2/2008 | Aranyi | |
| 7,334,718 B2 | 2/2008 | McAlister et al. | |
| 7,335,212 B2 | 2/2008 | Edoga et al. | |
| 7,364,060 B2 | 4/2008 | Milliman | |
| 7,398,908 B2 | 7/2008 | Holsten et al. | |
| 7,399,305 B2 | 7/2008 | Csiky et al. | |
| 7,401,721 B2 | 7/2008 | Holsten et al. | |
| 7,401,722 B2 | 7/2008 | Hur | |
| 7,407,075 B2 | 8/2008 | Holsten et al. | |
| 7,410,086 B2 | 8/2008 | Ortiz et al. | |
| 7,422,137 B2 | 9/2008 | Manzo | |
| 7,422,138 B2 | 9/2008 | Bilotti et al. | |
| 7,431,191 B2 | 10/2008 | Milliman | |
| 7,438,718 B2 | 10/2008 | Milliman et al. | |
| 7,455,676 B2 | 11/2008 | Holsten et al. | |
| 7,455,682 B2 | 11/2008 | Viola | |
| 7,481,347 B2 | 1/2009 | Roy | |
| 7,494,038 B2 | 2/2009 | Milliman | |
| 7,506,791 B2 | 3/2009 | Omaits et al. | |
| 7,516,877 B2 | 4/2009 | Aranyi | |
| 7,527,185 B2 | 5/2009 | Harari et al. | |
| 7,537,602 B2 | 5/2009 | Whitman | |
| 7,546,939 B2 | 6/2009 | Adams et al. | |
| 7,546,940 B2 | 6/2009 | Milliman et al. | |
| 7,547,312 B2 | 6/2009 | Bauman et al. | |
| 7,556,186 B2 | 7/2009 | Milliman | |
| 7,559,451 B2 | 7/2009 | Sharma et al. | |
| 7,585,306 B2 | 9/2009 | Abbott et al. | |

(56) References Cited

U.S. PATENT DOCUMENTS

| | | |
|---|---|---|
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,748,645 B2* | 7/2010 | Breese .............. A01M 7/005 180/315 |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,891,343 B2* | 2/2011 | Braun .............. F02M 55/002 123/446 |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,220,840 B2* | 7/2012 | Garraffa .............. B63C 11/205 128/201.27 |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,397,972 B2* | 3/2013 | Kostrzewski .... A61B 17/07207 227/175.2 |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,113,885 B2* | 8/2015 | Hodgkinson ....... A61B 17/1114 |
| 9,364,230 B2* | 6/2016 | Shelton, IV ...... A61B 17/07207 |
| 9,504,470 B2* | 11/2016 | Milliman .......... A61B 17/07292 |
| 9,506,592 B2* | 11/2016 | Turnau, III ........ F16L 37/0915 |
| 9,757,133 B2* | 9/2017 | Latimer ............. A61B 17/1155 |
| 9,845,907 B2* | 12/2017 | Hess ................... F16L 23/04 |
| 2003/0111507 A1 | 6/2003 | Nunez |
| 2004/0059227 A1 | 3/2004 | Nita et al. |
| 2004/0194324 A1 | 10/2004 | Youn-Chyuan |

(56) References Cited

U.S. PATENT DOCUMENTS

| | | |
|---|---|---|
| 2005/0051597 A1 | 3/2005 | Toledano |
| 2005/0107813 A1 | 5/2005 | Gilete Garcia |
| 2005/0236459 A1* | 10/2005 | Gresham .............. A61B 17/068 227/175.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0179375 A1 | 7/2008 | Scirica |
| 2008/0281299 A1* | 11/2008 | Menn .................. A61B 1/0014 606/1 |
| 2008/0308605 A1 | 12/2008 | Scirica |
| 2009/0078336 A1* | 3/2009 | Baudoux .............. B60K 15/04 141/311 R |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0326540 A1 | 12/2009 | Estes |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0253065 A1* | 10/2010 | Lotti .................. F16L 33/227 285/3 |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0095070 A1* | 4/2011 | Patel .................. A61B 17/115 227/181.1 |
| 2011/0114697 A1 | 5/2011 | Baxter, III et al. |
| 2011/0114700 A1 | 5/2011 | Baxter, III et al. |
| 2011/0132964 A1* | 6/2011 | Weisenburgh, II .......... A61B 17/07207 227/176.1 |
| 2011/0144640 A1 | 6/2011 | Heinrich et al. |
| 2011/0147432 A1 | 6/2011 | Heinrich et al. |
| 2011/0186614 A1 | 8/2011 | Kasvikis |
| 2011/0192882 A1 | 8/2011 | Hess et al. |
| 2011/0205072 A1* | 8/2011 | Ben-Mansour ....... G01M 3/183 340/605 |
| 2011/0276036 A1 | 11/2011 | Spranger et al. |
| 2012/0061448 A1 | 3/2012 | Zingman |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0056517 A1* | 3/2013 | Patel .................. A61B 17/115 227/175.2 |
| 2013/0060258 A1 | 3/2013 | Giacomantonio |
| 2013/0096591 A1 | 4/2013 | Hart et al. |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0123705 A1 | 5/2013 | Holm et al. |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0158566 A1* | 6/2013 | Harris ................ A61B 17/1285 606/142 |
| 2013/0167365 A1* | 7/2013 | Herren ..................... F16L 1/06 29/700 |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181029 A1 | 7/2013 | Milliman |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0200607 A1* | 8/2013 | Rodenberg .......... F16L 37/0915 285/82 |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0001236 A1* | 1/2014 | Shelton, IV ...... A61B 17/07207 227/176.1 |
| 2014/0008413 A1 | 1/2014 | Williams |
| 2014/0012317 A1 | 1/2014 | Orban et al. |
| 2014/0025071 A1* | 1/2014 | Sims .................. A61B 18/1445 606/46 |
| 2014/0309677 A1 | 10/2014 | Baldwin |
| 2014/0312095 A1* | 10/2014 | Scirica ............. A61B 17/07207 227/176.1 |
| 2014/0373652 A1* | 12/2014 | Zergiebel ................ F16H 19/02 74/89.23 |
| 2015/0108201 A1 | 4/2015 | Williams |
| 2015/0320420 A1 | 11/2015 | Penna et al. |
| 2016/0157856 A1* | 6/2016 | Williams .............. A61B 17/068 227/175.1 |
| 2016/0175026 A1* | 6/2016 | Bhagat ................ A61B 18/1445 606/52 |
| 2016/0192934 A1* | 7/2016 | Williams .............. A61B 17/105 227/176.1 |
| 2016/0192938 A1* | 7/2016 | Sgroi, Jr. ........... A61B 17/1155 227/175.1 |
| 2016/0245443 A1* | 8/2016 | Zonneveld ................ F16L 37/18 |
| 2016/0279279 A1* | 9/2016 | Wonnacott .............. A61L 9/048 |
| 2017/0079660 A1* | 3/2017 | Sgroi .................. A61B 17/068 |
| 2017/0198887 A1* | 7/2017 | Veloskey ................ F21V 17/02 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1190796 A1 | 3/2002 |
| EP | 1354560 A2 | 10/2003 |
| EP | 1631199 A1 | 3/2006 |
| EP | 2090245 A1 | 8/2009 |
| EP | 2524656 A2 | 11/2012 |
| EP | 2774549 A2 | 9/2014 |
| EP | 3042619 A1 | 7/2016 |
| FR | 1136020 A | 5/1957 |

(56) References Cited

FOREIGN PATENT DOCUMENTS

| | | | |
|---|---|---|---|
| FR | 1461464 | A | 2/1966 |
| FR | 1588250 | A | 4/1970 |
| FR | 2243758 | A1 | 4/1975 |
| FR | 2443239 | A1 | 7/1980 |
| GB | 1185292 | A | 3/1970 |
| GB | 2016991 | A | 9/1979 |
| GB | 2070499 | A | 9/1981 |
| NL | 7711347 | A | 4/1979 |
| SU | 1509052 | A1 | 9/1989 |
| WO | 8706448 | A1 | 11/1987 |
| WO | 8900406 | A1 | 1/1989 |
| WO | 9006085 | A1 | 6/1990 |
| WO | 9805261 | A2 | 2/1998 |
| WO | 2001/054594 | A1 | 8/2001 |
| WO | 2004107990 | A1 | 12/2004 |
| WO | 2008/107918 | A1 | 9/2008 |
| WO | 2012015917 | A1 | 2/2012 |
| WO | 2014139327 | A1 | 9/2014 |
| WO | 2014139440 | A1 | 9/2014 |
| WO | 2014139442 | A1 | 9/2014 |
| WO | 2014139467 | A1 | 9/2014 |
| WO | 20140139442 | A1 | 9/2014 |

OTHER PUBLICATIONS

European Search Report dated Sep. 1, 2016, issued in EP 16166326.
European Search Report dated May 10, 2016, issued in EP Application No. 15 19 8203.
European Search Report dated May 17, 2016, issued in EP Application No. 16 15 0284.
European Search Report dated Jun. 24, 2016, issued in EP Application No. 16150288.5.
U.S. Appl. No. 14/591,193, filed Jan. 7, 2015, inventor: Sgroi, Jr.
U.S. Appl. No. 14/810,811, filed Jul. 28, 2015, inventor: Sgroi, Jr., et al.
U.S. Appl. No. 14/859,590, filed Sep. 21, 2015, inventor: Sgroi.
U.S. Appl. No. 62/100,512, filed Jan. 7, 2015, inventor: Williams et al.
U.S. Appl. No. 62/150,913, filed Apr. 22, 2015, inventor: Penna et al.
U.S. Appl. No. 14/804,814, filed Jul. 21, 2015, inventor: Williams.
Partial European Search Report dated Jan. 16, 2017, issued in EP Appln. No. 16180339.
European Search Report dated Apr. 20, 2017, issued in EP Application No. 16180339.
European Search Report dated Nov. 30, 2016, issued in EP Application No. 16181395.
EP Examination Report dated Jun. 20, 2017, issued in EP Application No. 16150288.

* cited by examiner

LOADING UNIT LOCKING BAND FOR SURGICAL STAPLING INSTRUMENT

BACKGROUND

1. Technical Field

The present disclosure relates generally to surgical stapling instruments. More specifically, the present disclosure relates to circular stapling instruments having replaceable loading units.

2. Background of Related Art

Surgical stapling instruments configured to join tissue portions during a surgical procedure are well known. These instruments include linear end effectors which are oriented parallel or transverse to a longitudinal axis of the instrument. These instruments also include circular end effectors. Typically, the linear stapling instruments include a disposable loading unit or a replaceable cartridge that allows the stapling instrument to be used multiple times. In contrast, conventional circular stapling instruments typically include a cartridge or shell assembly that is fixedly attached to the instrument such that the instrument must be disposed of after a single use.

A need exists in the art for a simple, inexpensive instrument for releasably, but securely, fastening a cartridge or shell assembly to a circular stapling instrument to facilitate reuse of the stapling instrument.

SUMMARY

In an aspect of the present disclosure, a loading unit includes a shell assembly and a locking band. The shell assembly has a proximally extending annular body. The annular body defines two hook openings that oppose one another, a lug opening positioned between the hook openings, and a central passage for receiving a portion of a surgical instrument. The locking band has an arced body with two ends, a retention hook positioned adjacent each end of the body and extending from the inner surface of the body. Each of the retention hooks is disposed within a respective one of the hook opening to retain a respective one of the ends of the locking band to the annular body. The lug is disposable through the lug opening into the central passage to secure the loading unit to a surgical instrument.

In aspects, each of the retention hooks has a disengaged configuration. When both of the retention hooks are in the disengaged configuration, the lug may extend through the lug opening into the central passage. Each end of the body may be moveable to move a respective one of the retention hooks towards an engaged configuration such that a portion of the retention hook engages the annular body between the respective hook opening and the lug window. Movement of the retention hooks towards the engaged position may cause the lug to be lifted outside of the central passage of the annular body to release a portion of the surgical instrument from the locking band.

In some aspects, the lug opening is positioned halfway between the hook openings. The lug may be positioned halfway between the retention hooks. The annular body may define a recess between the hook openings. The recess may be configured to receive the body of the locking band. The locking band may include a tab that extends distally from the body. The shell assembly may define a tab receiver that is in communication with the recess. The tab receiver may be configured to receive the tab of the locking band to radially align the locking band to the shell assembly. The tab may be axially aligned with the lug.

In certain aspects, the annular body includes flats adjacent each hook opening. The flats may define planes that are parallel to one another. Each end of the locking band may have a linear inner surface that slidably engages a respective one of the flats of the annular body. Each of the retention hooks may extend inward from a respective one of the liner inner surfaces. Each end of the locking band may also include a detent that extends inwardly from the respective linear inner surface that is positioned away from the retention hook and the lug. Each of the flats of the annular body may define a detent well. Each of the detent wells may be configured to receive a respective one of the detents. In a locked configuration of the locking band, each detent of the locking band may be received within a respective one of the detent wells and the lug may be positioned through the lug opening into the central passage. In an unlocked configuration of the locking band, each detent of the locking band may be received within a respective one of the detent walls and the lug may be positioned outside of the central passage. In a released configuration of the locking band, at least one of the detents may be disposed within a respective one of the hook openings and the lug may be positioned outside of the central passage.

In another aspect of the present disclosure, a loading unit includes a shell assembly and a locking band. The shell assembly has a proximally extending annular body. The annular body defines two detent walls that are defined in an outer surface of the annular body spaced from one another, a lug opening extending through the annular body, and a central passage that receives a distal end portion of a surgical instrument. The locking band has an arced body with two ends. Each end of the arced body has a detent that extends from an inner surface of the body. The body includes an inwardly extending lug that is positioned between the ends. In a locked configuration of the body, each detent is received within a respective detent wall and the lug extends through the lug opening and into the central passage. In an unlocked configuration of the body, each detent is received within a respective detent well and the lug is positioned outside of the central passage. In a released configuration of the body, at least one detent is positioned about the annular body between a respective detent well and the lug opening and the lug is positioned outside of the central passage.

In aspects, the annular body defines two flats that are parallel to one another on opposite sides of the annular body. A respective one of the detent wells may be defined in each of the flats. The shell assembly may define a hook opening between each of the detent walls and the lug opening. The locking band may include an inwardly extending retention hook that is positioned between each of the detents and the lug. The retention hooks may be configured to engage the annular body in the released configuration to secure a respective one of the ends of the locking band to the annular body. In the released configuration at least one of the detents is positioned in a respective one of the hook openings. The annular body may define two flats that are parallel to one another on opposite sides of the annular body. A respective one of the detent well and a respective one of the hook openings may be defined in each of the flats.

In another aspect of the present disclosure, a surgical system includes a surgical instrument, a loading unit, and a locking band. The surgical instrument has a distal end portion that defines a lug opening. The loading unit includes a shell assembly that has a proximally extending annular body. The annular body defines two hook opening that oppose one another, a lug opening that is positioned between the hook openings, and a central passage that receives the distal end portion of the surgical instrument. The locking band has an arced body with two ends, a retention hook that is positioned adjacent each end of the body and extending from an inner surface of the body, and a lug that is positioned between the retention hoods and extending from the inner surface of the body. Each of the retention hooks is disposed within a respective one of the hook openings to retain a respective one of the ends of the locking band to the annular body. In a locked configuration of the body, the lug is disposed through the lug opening of the annular body and the lug window of the surgical instrument to secure the loading unit to the distal end portion of the surgical instrument.

In aspects, the annular body includes a key that extends from an inner surface and is parallel to a longitudinal axis of the shell assembly. The distal end portion of the surgical instrument may define a keyway that is parallel to a longitudinal axis of the distal end portion. The keyway may slidably receive the key to rotatably align and fix the shell assembly to the distal end portion of the surgical instrument. The distal end portion may define hook windows that oppose one another. Each of the hook windows may receive one of the retention hooks of the locking band.

In another aspect of the present disclosure, a method of providing a surgical instrument includes aligning a loading unit with a surgical instrument and sliding an annular body of the loading unit of a distal end portion of the surgical instrument. Aligning the loading unit with the surgical instrument includes aligning a longitudinal axis of the loading unit with a longitudinal axis of the distal end portion of the surgical instrument. When the loading unit and the surgical instrument are aligned, a lug opening defined through the annular body of a shell assembly of the loading unit is radially aligned with a lug windows defined through the distal end portion of the surgical instrument. When the annular body of the loading unit is slid over the distal end portion of the surgical instrument, the distal end portion engages a lug of a locking band that is disposed about the annular body to move the lug outwards as the loading unit slides over the distal end portion until the lug windows is aligned with the lug opening. Resilience of the body of the locking band snaps the lug through the lug window when the lug windows and the lug opening are longitudinally aligned to secure the loading unit to the distal end portion of the surgical instrument. The locking band has an arced body that includes a detent positioned adjacent each end. Each detent extends inward and is selectively received within a respective detent well defined in the annular body to fix the end of the body to the annular body as the annular body slides over the distal end portion of the surgical instrument.

In aspects, the method may include releasing the loading unit from the distal end portion of the surgical instrument. Moving one of the ends of the body of the locking band towards the lug may slide the end relative to the annular body such that the detent disengages the respective detent well. The body may flex in response to moving the end of the body to move the lug out of the locking window so that distal end portion of the surgical instrument. When the lug out of the locking window of the distal end portion of the surgical instrument the method may include removing the loading unit from over the distal end portion of the surgical instrument.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION OF EMBODIMENTS

Figure 1:
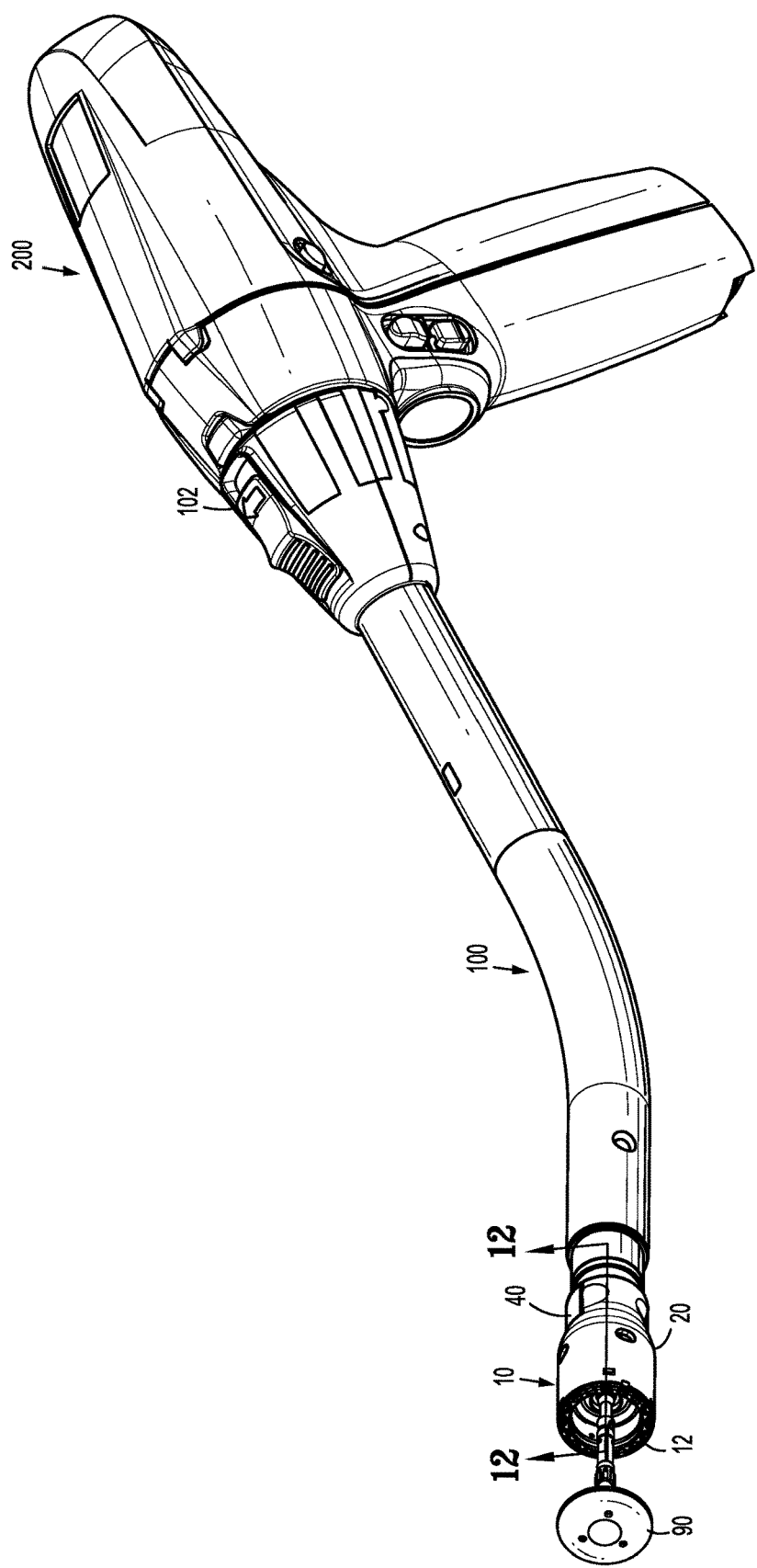
FIG. 1 is a perspective view of a surgical system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to a loading unit having a locking band that releasably secures the loading unit to the distal end portion of a surgical instrument or adapter for a surgical instrument. The locking band has a detent and a retention hook adjacent each end of the locking band that prevent the locking band from detaching from the loading unit when the loading unit is secured and released from the distal end portion of the surgical instrument.

Figure 2:
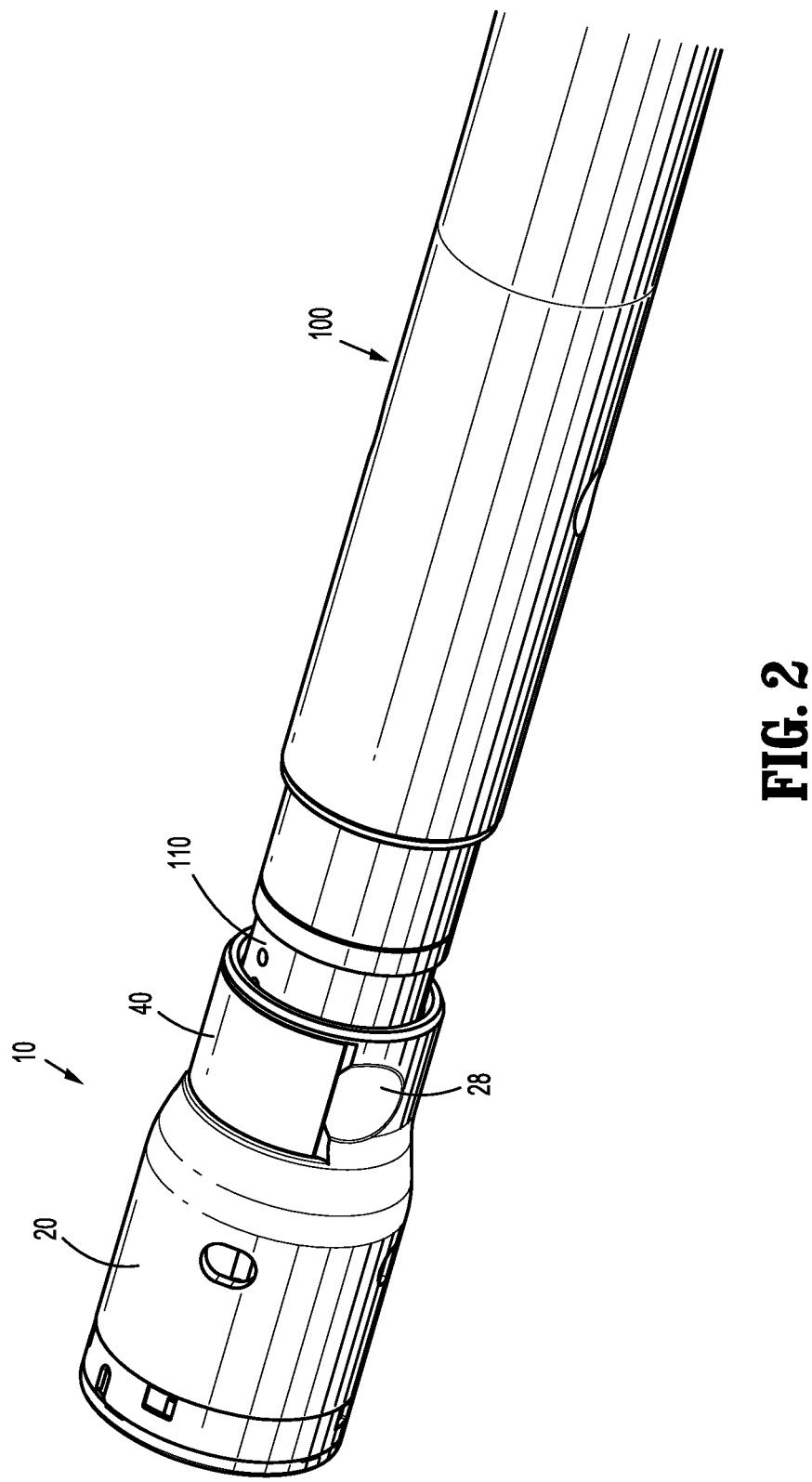
FIG. 2 is a perspective view of a distal end portion of the surgical system shown in FIG. 1 including a loading unit coupled to an adapter.

FIGS. 1 and 2 illustrate a loading unit 10 and an adapter 100 in accordance with an embodiment of the present disclosure. The loading unit 10 is configured for selective connection to a powered hand held electromechanical instrument 200 via the adapter 100. Alternatively, the loading unit 10 can be configured for connection to a manually actuated handle assembly or stapling instrument such as described in U.S. Pat. No. 8,789,737 ("the '737 patent"), which is incorporated herein by reference. In such an embodiment, an elongated body portion of the stapling instrument may have a configuration similar to that of the adapter 100 as shown in FIG. 1. In the illustrated embodiment, the loading unit 10 is releasably coupled to a distal end portion 110 of the adapter 100 and includes a staple cartridge 12, a shell assembly 20, and an attachment member or locking band 40 for releasably securing the loading unit 10 to the adapter 100. The loading unit 10 may also include an anvil 90. The adapter 100 is configured to translate movement of a stapling instrument, e.g., an electromechanical instrument 200, to actuate the shell assembly 20, to effect approximation of the anvil 90 and the staple cartridge 12, and to suture and cut tissue (not shown). A proximal end 102 of the adapter 100 is attachable to the stapling instrument to actuate the staple cartridge 12. It is contemplated that the proximal end 102 of the adapter 100 may be attached to a manually actuated instrument such as described in the '737 patent to actuate the staple cartridge 12.

For a detailed description of the structure and function of an exemplary adapter and loading unit, please refer to commonly owned U.S. Provisional Patent Application Ser. No. 62/066,518, filed Oct. 21, 2014, and entitled "Adapter, Extension, and Connector Assemblies for Surgical Devices." For a detailed description of the structure and function of an exemplary electromechanical instrument, please refer to commonly owned U.S. patent application Ser. No. 13/484,975, filed on May 31, 2012, now published as U.S. Patent Publication No. 2012/0253329. Each of these applications is incorporated herein by reference in its entirety.

Figure 3:
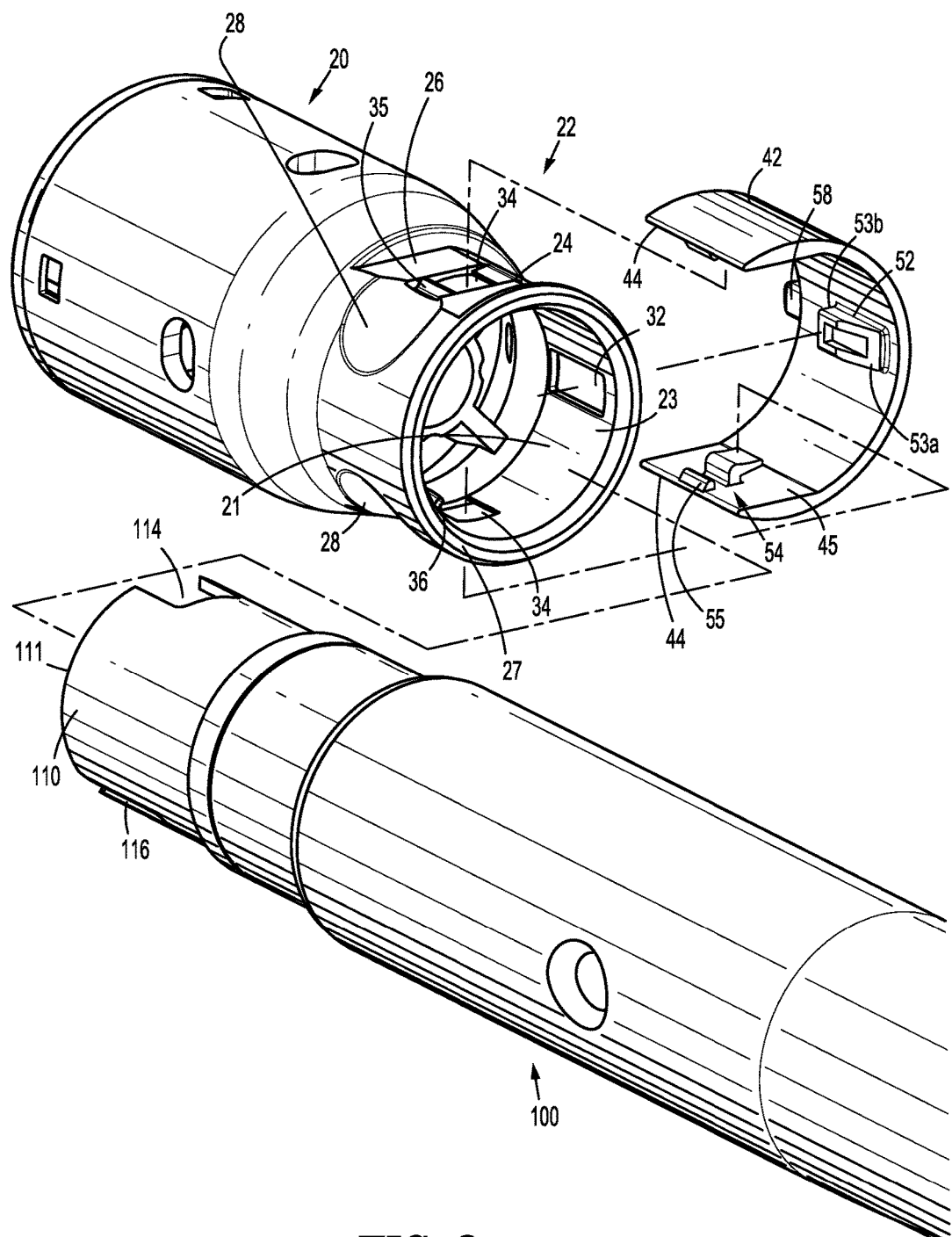
FIG. 3 is a perspective, exploded view from the proximal end of the loading unit and the distal end portion of the adapter of FIG. 2.
Figure 4:
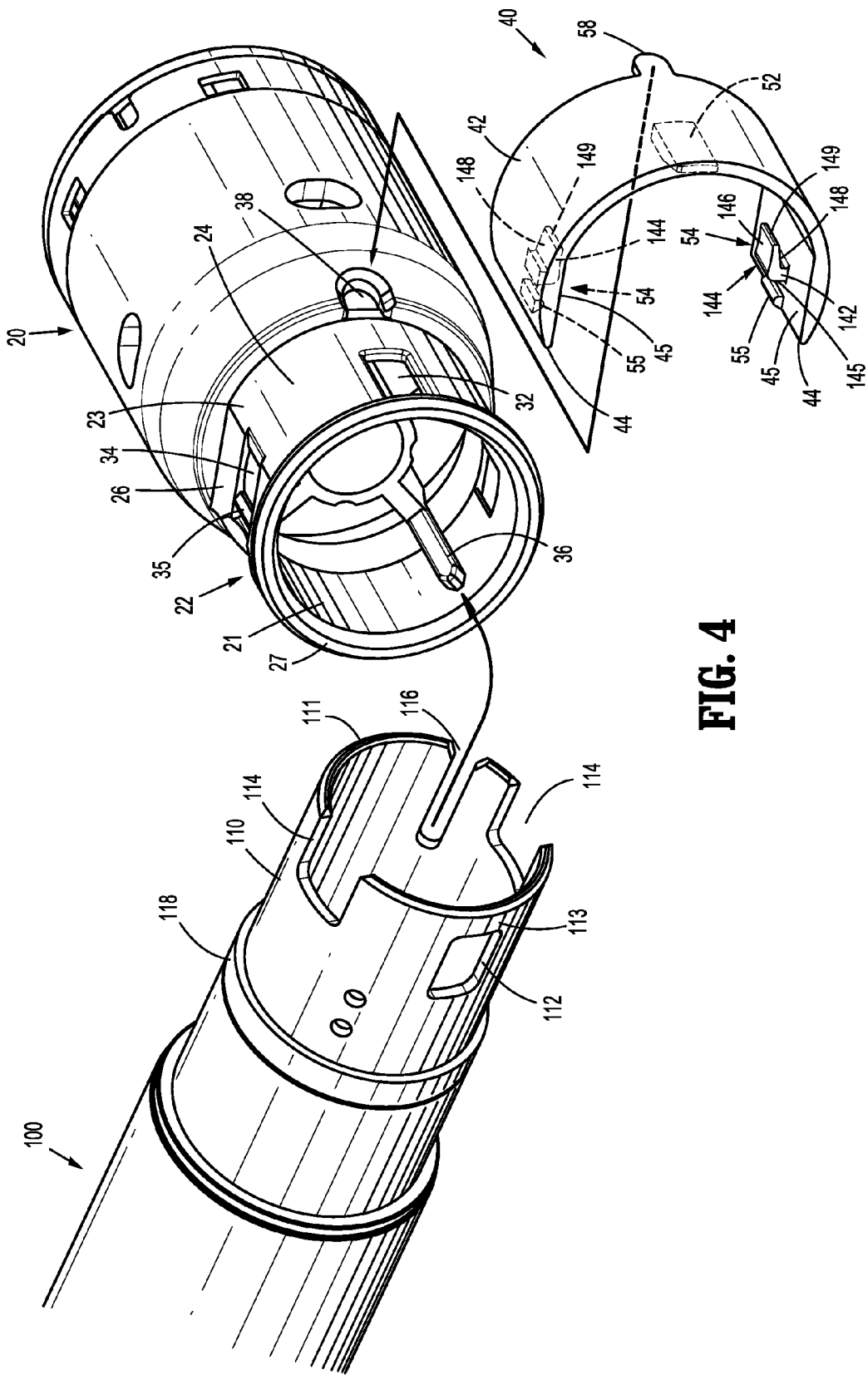
FIG. 4 is an exploded view of the loading unit and the distal end portion of the adapter of FIG. 2.

With reference to FIGS. 3 and 4, the distal end portion 110 of the adapter 100 or surgical instrument is tubular and defines a lug window 112 (FIG. 4), hook windows 114, and a keyway 116. The lug window 112 extends through the distal end portion 110 and is spaced apart from a distal end 111 of the distal end portion 110 by a lift section 113. The hook windows 114 extend proximally from the distal end 111 of the distal end portion 110 in a direction parallel to a longitudinal axis of the distal end portion 110. The distal end portion 110 defines two hook windows 114 each positioned an equal distance from the lug window 112 in opposite directions from one another about the distal end portion 110. Each of the hook windows 114 may be offset approximately 90° about the distal end portion 110 away from the lug window 112 such that the hook windows 114 diametrically oppose one another. The keyway 116 is positioned between the hook windows 114 on a side of the distal end portion 110 opposing the lug window 112. As shown, the keyway 116 is adjacent one of the hook windows 114 and is spaced apart from the other one of the hook windows 114; however, it is contemplated that the keyway 116 may be equally spaced between the hook windows 114 such that the keyway 116 opposes the lug window 112. The keyway 116 extends proximally from the distal end 111 of the distal end portion 110 in a direction parallel to the longitudinal axis of the distal end portion 110. The adapter 100 includes a proximal stop 118 positioned about a proximal end of the distal end portion 110 of the adapter 100. The proximal stop 118 has a diameter greater than the distal end portion 110 and is positioned to abut a proximal end of the shell assembly 20 when the shell assembly 20 is positioned on the adapter 100.

The shell assembly 20 has a proximal portion 22 that defines a central passage 21 for receiving the distal end portion 110 of the adapter 100 as detailed below. The proximal portion 22 includes an annular body 23 that defines an annular recess 24. The annular recess 24 extends about one half of the circumference of the annular body 23 and includes flats 26 at each end of the annular recess 24. The flats 26 are substantially parallel with one another and are positioned approximately 180° apart from one another on the annular body 23. The shell assembly 20 also includes a retaining or proximal ring 27 that has a constant diameter equal to or greater than a diameter of the annular body 23.

The annular body 23 includes a key 36 and defines a lug opening 32, hook openings 34, and a tab receiver 38. The lug opening 32 passes through the annular body 23 and is positioned within the annular recess 24 approximately halfway between the flats 26. The hook openings 34 pass through the flats 26 of the annular body 23 transverse to a longitudinal axis of the shell assembly 20. Each flat 26 defines a detent groove or detent well 35 that is spaced apart from the hook opening 34 and positioned away from the annular recess 24. The tab receiver 38 is defined in the proximal portion 22 of the shell assembly 20 distal to and in communication with the annular recess 24. The tab receiver 38 is aligned with lug opening 32 and extends distally from the annular recess 24 in a direction parallel to a longitudinal axis of the shell assembly 20. The key 36 extends from an inner surface 23 of the annular body 23 between the hook openings 24. The proximal portion 22 may also define engagement recesses 28 (FIG. 3) adjacent the flats 26 and positioned away from the annular recess 24.

The locking band 40 includes a body 42 having ends 44, a lug 52, retention hooks 54, detents 55, and a tab 58. The body 42 is arced or semi-cylindrical in shape and is sized to be received within the annular recess 24 about the annular body 23 of the shell assembly 20. The lug 52 is positioned approximately halfway between the ends 44 and extends from an inner surface of the body 42. The lug 52 includes an angled proximal surface 53a and a vertical distal locking surface 53b such that the lug 52 is substantially wedge shaped.

Each end 44 of the body 42 has a linear or flat inner surface 45 that is substantially parallel to the flat inner surface 45 of the opposing end 44. Each retention hook 54 is positioned adjacent an end 44 of the body 42 and extends inward from the flat inner surface 45. Each retention hook 54 includes a support member 142 and a hook member 144. The support member 142 extends orthogonally from the flat inner surface 45 towards the opposing flat inner surface 45. The hook member 144 extends substantially parallel to the flat inner surface 45 towards the lug 52. The hook member 144 includes a flat outer surface 146 that opposes the flat outer surface 146 of the hook member 144 of the other retention hook 54 and an angled inner surface 148 that opposes the flat inner surface 45 of the end 44. The hook member 144 is substantially wedge shaped with a leading end 149 of the hook member 144 having a smaller dimension than a trailing end 145 of the hook member 144. Each end 44 also includes a detent 55 protruding from the flat inner surface 45 and positioned adjacent the support member 142 of the retention hook 54 and away from the lug 52. The tab 58 extends distally from the body 42 in a direction parallel to a longitudinal axis of the shell assembly 20 when the body 42 is received within the annular recess 24. The tab 58 is axially aligned with the lug 52 and is sized to be received within the tab receiver 38 to index or align the locking band 40 with the shell assembly 20.

With additional reference to FIGS. 5 and 6, the body 42 of the locking band 40 is receivable within the recess 24 of the annular body 23 of the shell assembly 20 to selectively secure the shell assembly 20 to the distal end portion 110 of the adapter 100 (FIG. 1) as described in greater detail below. When the body 42 of the locking band 40 is received within the recess 24, the tab 58 indexes or aligns the body 42 with the proximal portion 22 of the shell assembly 20 such that the lug 52 is aligned with the lug opening 32 and each retention hook 54 is aligned with a respective hook opening 34. The tab 58 provides visual indicia as to the proper alignment of the body 42 with the annular body 23. When the lug 52 is received within the lug opening 32, the locking band 40 is prevented from rotating relative to the shell assembly 20.

Figure 5:
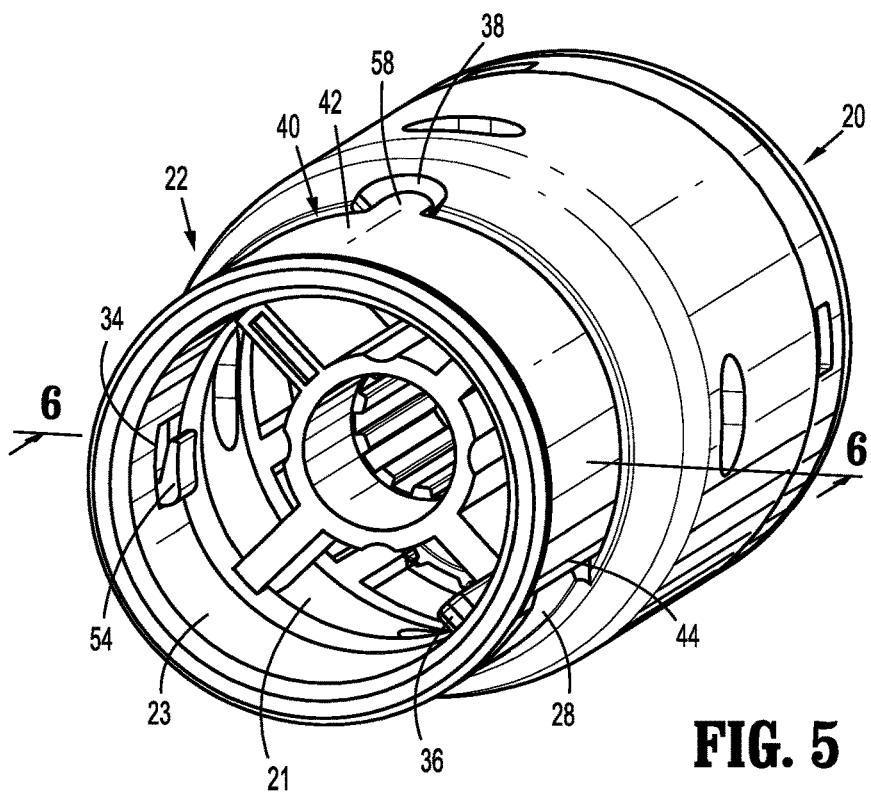
FIG. 5 is a perspective view from the proximal end of the loading unit of FIG. 2.
Figure 6:
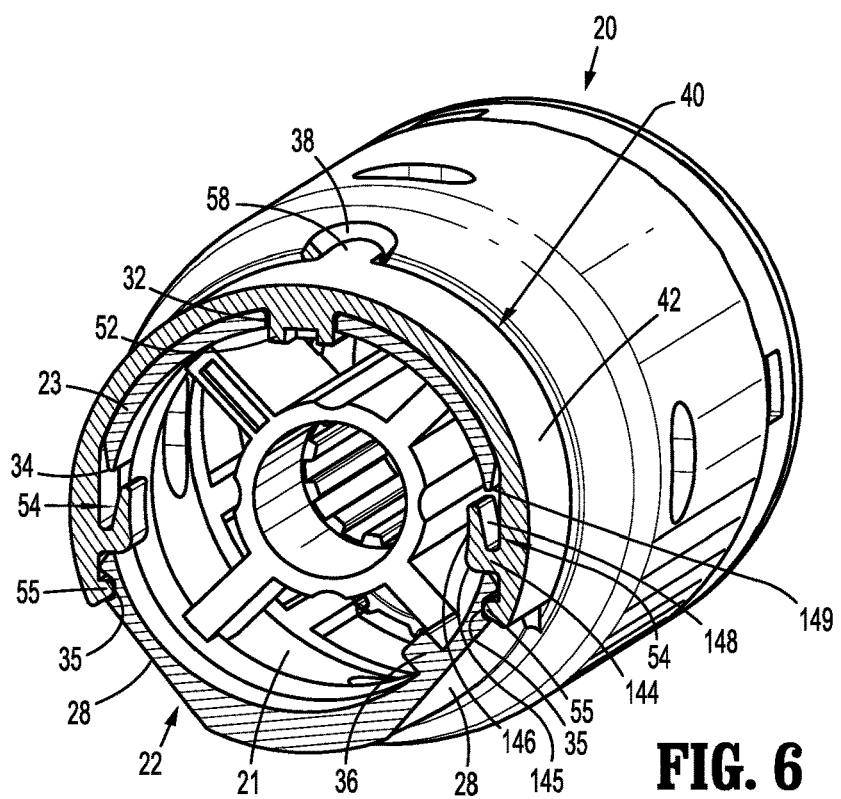
FIG. 6 is a cross-sectional view taken along the section line 6-6 of FIG. 5.
Figure 7:
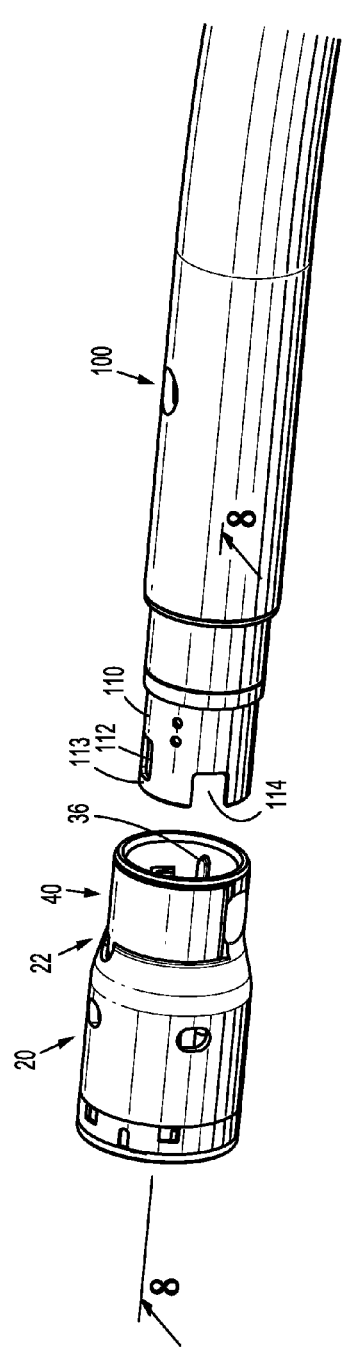
FIG. 7 is a side view of the loading unit of FIG. 2 aligned with the distal end portion of the adapter of FIG. 2 with a locking band of the loading unit in a locked configuration.
Figure 8:
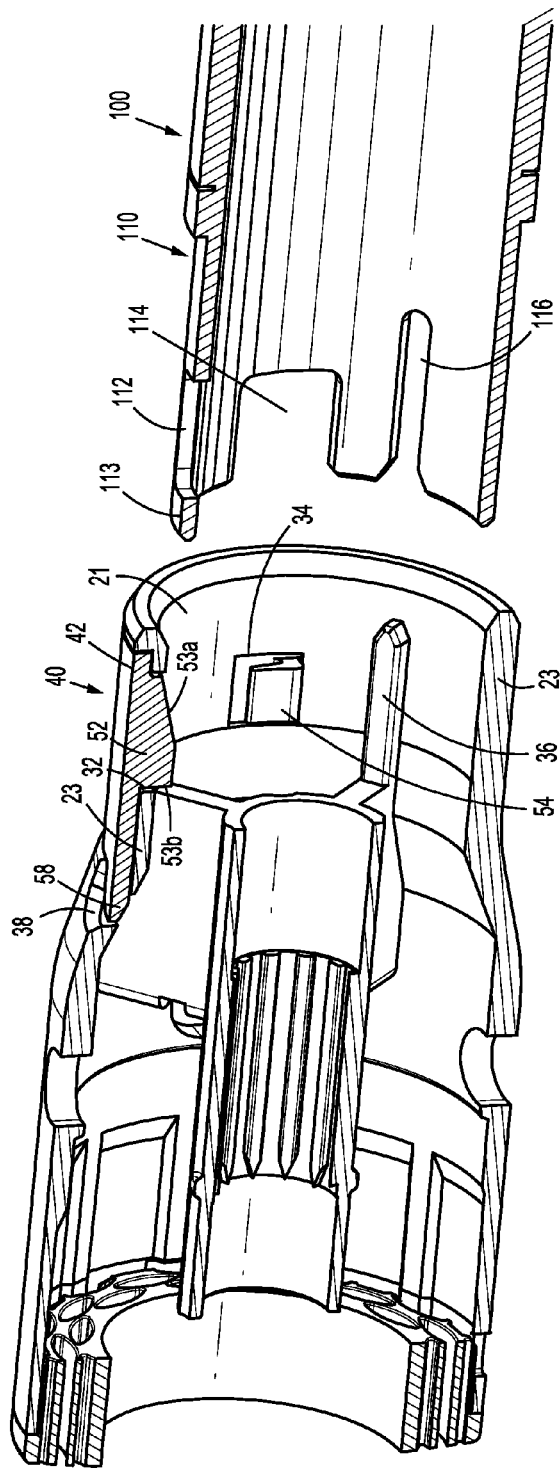
FIG. 8 is a cross-sectional view taken along the section line 8-8 of FIG. 7.

With continued reference to FIGS. 5 and 6, the retention hooks 54 are in a disengaged configuration within the hook openings 34. In the disengaged position, the trailing end 145 of the retention hooks 54 are adjacent to or in contact with a wall defining the respective hook opening 34 such that the support member 142 is adjacent or in contact with the wall defining the respective hook opening 34. In the disengaged position, the detents 55 are received in the detent wells 35 to prevent the respective end 44 of the body 42 from moving or sliding relative to the annular body 23. In the disengaged configuration, a respective end 44 of the body 42 may be engaged with a clinician's finger to slide the end 44 in the direction of the lug 52. This movement causes the body 42 of the locking band 40 to flex outwardly to lift a respective detent 55 from its detent well 35 and withdraw a respective retention hook 54 from its hook opening 34.

To selectively couple the locking band 40 to the proximal portion 22 of the shell assembly 20 as shown in FIGS. 5 and 6, the locking band 40 is aligned with the proximal portion 22 by placing the inner flats 45 on the flats 26 of the proximal portion 22. When the inner flats 45 and the flats 26 of the annular body 23 are in contact with one another, alignment of the tab 58 and the tab recess 38 is visually verified to ensure the body 42 of the locking band 40 is in proper alignment with the annular body 23. When the body 42 is properly aligned with the annular body 23, pressure is applied to the body 42 such that the ends 44 of the body 42 slide over the flats 26 and the detents 55 engage the respective flats 26 to flex the body 42 outward. As the ends 44 slide over the flats 26, the retention hooks 54 engage the flats 26 to flex the ends 44 of the body 42 outward until the retention hooks 54 become aligned with the hook opening 34. When the retention hooks 54 becomes aligned with the hook openings 34, the resiliency of the body 42 snaps or flexes the ends 44 inward such that the retention hooks 54 pass through the hook openings 34 and the detent 55 reengages the flat 26 past the hook opening 34. Additional pressure on the body 42 slides the detent 55 along the flat 26 until the detent 55 is received within the detent well 35 as shown in FIG. 6. When the detent 55 is received within the detent well 35, the detent 55 may provide audible indicia, e.g., a "click," to indicate to a clinician that the locking band 40 is secured to the annular body 23 of the shell assembly 20. When the detents 55 are received in the detent wells 35 and the lug 52 passes through the lug opening 32 and into the central passage 21, the locking band 40 is in a locked configuration.

With reference to FIGS. 7-13, the locking band 40 is used to selectively secure the shell assembly 20 to the distal end portion 110 of the adapter 100 or surgical instrument as described in detail below. Initially referring to FIGS. 7 and 8, to secure the shell assembly 20 to the adapter 100, the longitudinal axis of the shell assembly 20 is aligned with the longitudinal axis of the distal end portion 110 of the adapter 100 with the locking band 40 coupled to the shell assembly 20. The shell assembly 20 is indexed or radially aligned with the distal end portion 110 of the adapter 100 such that the key 36 of the annular body 23 is aligned with the keyway 116 of the distal end portion 110. When the shell assembly 20 is radially aligned with the distal end portion 110 of the adapter 100, the lug window 112 of the distal end portion 110 is radially aligned with the lug opening 52 of the shell assembly 20 and the hook windows 114 of the distal end portion 110 are radially aligned with the hook openings 54 of the shell assembly 34.

Figure 9:
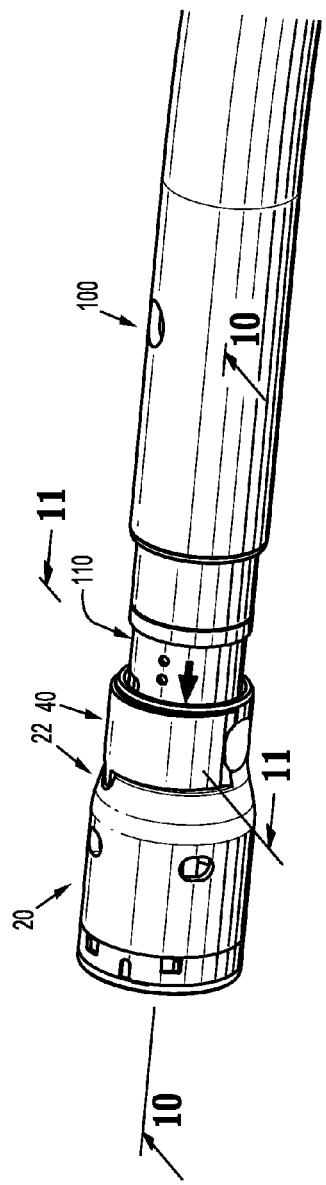
FIG. 9 is a side view of the distal end portion of the adapter of FIG. 7 partially received within the loading unit of FIG. 7 with the locking band in an unlocked configuration.
Figure 10:
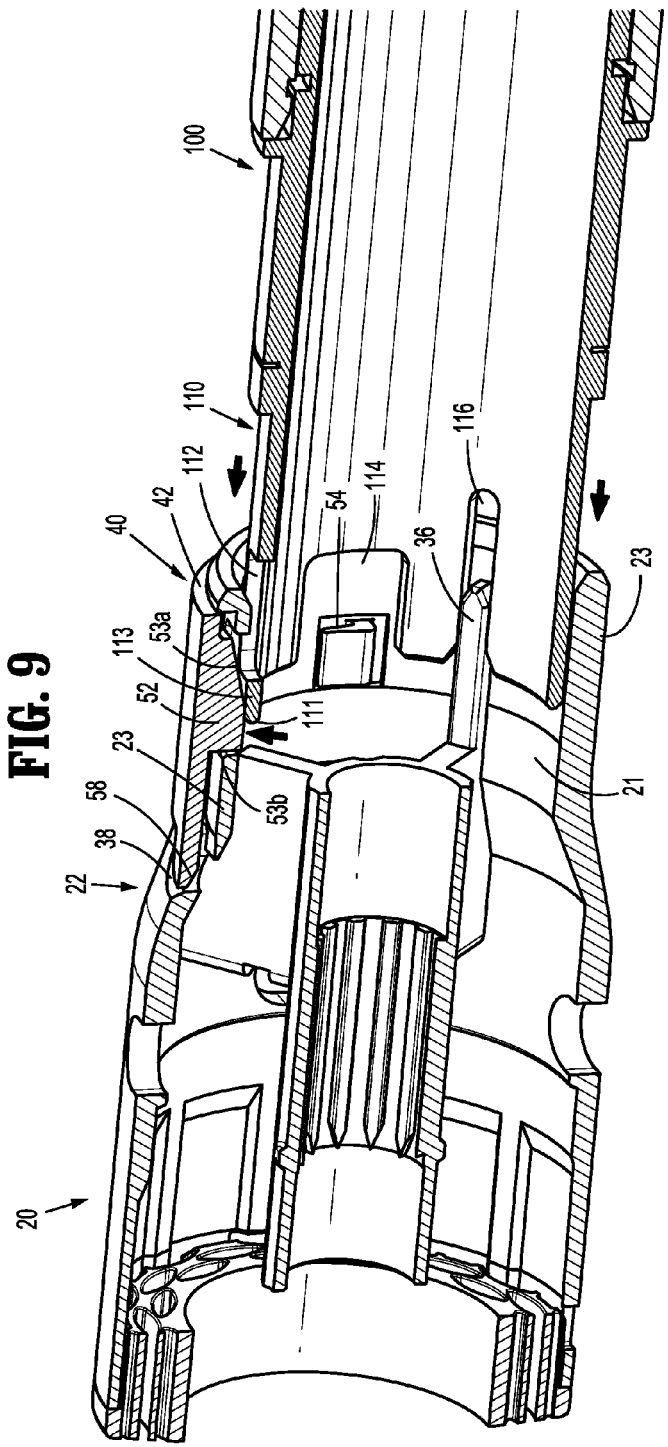
FIG. 10 is a cross-sectional view taken along the section line 10-10 of FIG. 9.
Figure 11:
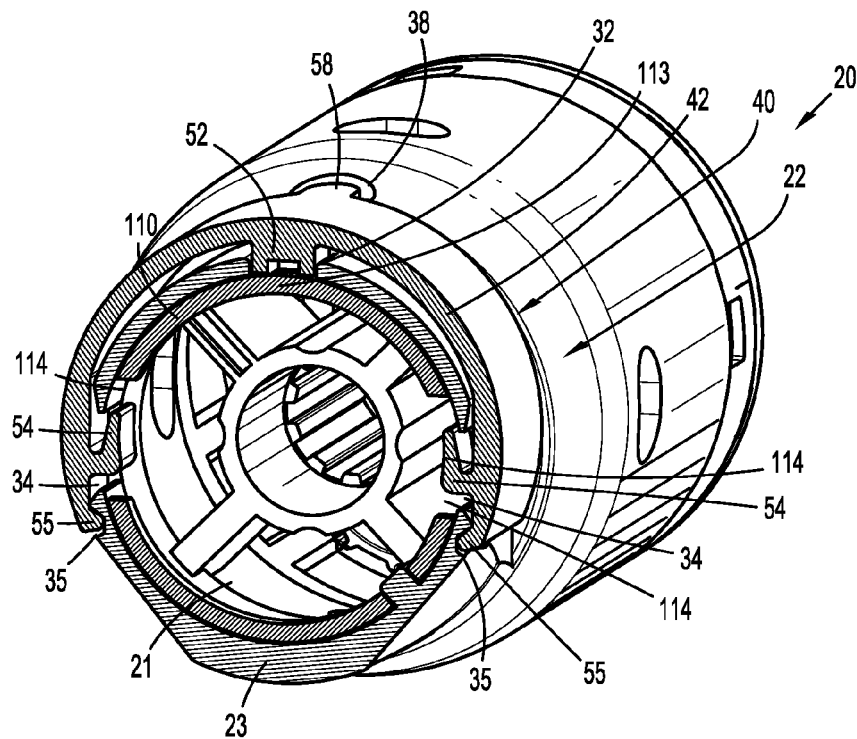
FIG. 11 is a cross-sectional view taken along the section line 11-11 of FIG. 9.

Referring to FIGS. 9-11, when the shell assembly 20 and the distal end portion 110 of the adapter 100 are longitudinally and radially aligned with one another, the annular body 23 of the shell assembly 20 is slid over the distal end portion 110. As distal end portion 110 is received within the central passage 21 of the annular body 23, the key 36 is received within the keyway 116 of the distal end portion 110 to radially fix the shell assembly 20 with the distal end portion 110 of the adapter 100. As the annular body 23 of the shell assembly 20 slides over the distal end portion 110 of the adapter 100, the lift section 113, which is positioned between the distal end 111 of the distal end portion 110 and the lug window 112, engages the lug 52 of the locking band 40 to transition the locking band 40 from the locked configuration to an unlocked configuration. Specifically, the lift section 113 engages the angled proximal surface 53a of the lug 52 to flex the body 42 outwardly to move the lug 52 outward until the lug 52 is positioned outside of the central passage 21 as shown in FIGS. 10 and 11.

With particular reference to FIG. 11, in the unlocked configuration, the detents 55 of the locking band 40 remain disposed within the detent wells 35 of the annular body 23 with the lug 52 positioned outside of the central passage 21. As shown, the body 42 of the locking band 40 flexes outward between the ends 44 of the locking band 40 as the lug 52 moves from within the central passage 21. The retention hooks 54 may also engage walls defining the hook openings 34 to prevent the locking band 40 from decoupling or detaching from the annular body 23 of the shell assembly 20. Specifically, the hook member 144 may capture the wall defining the hook opening 34 towards the lug 52 to secure the locking band 40 to the annular body 23 even if one or both of the detents 55 is released from within a respective detent well 35.

Figure 12:
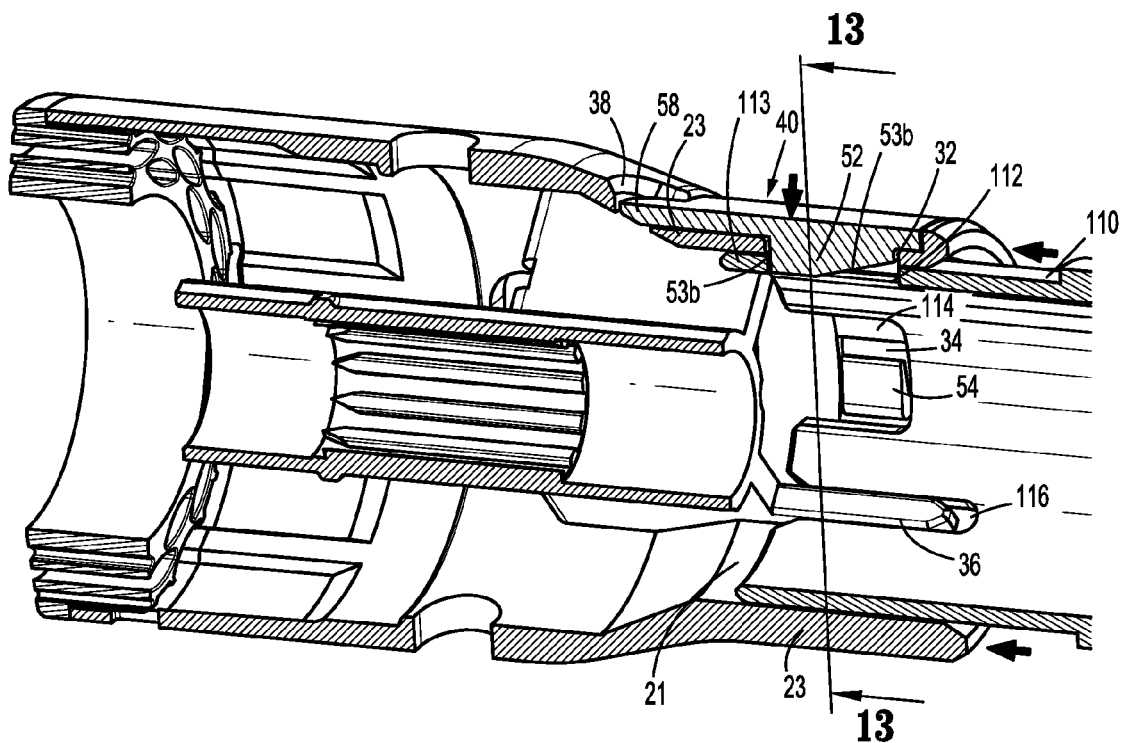
FIG. 12 is a cross-sectional view taken along the section line 12-12 of FIG. 1 with the locking band in the locked configuration and the anvil removed.
Figure 13:
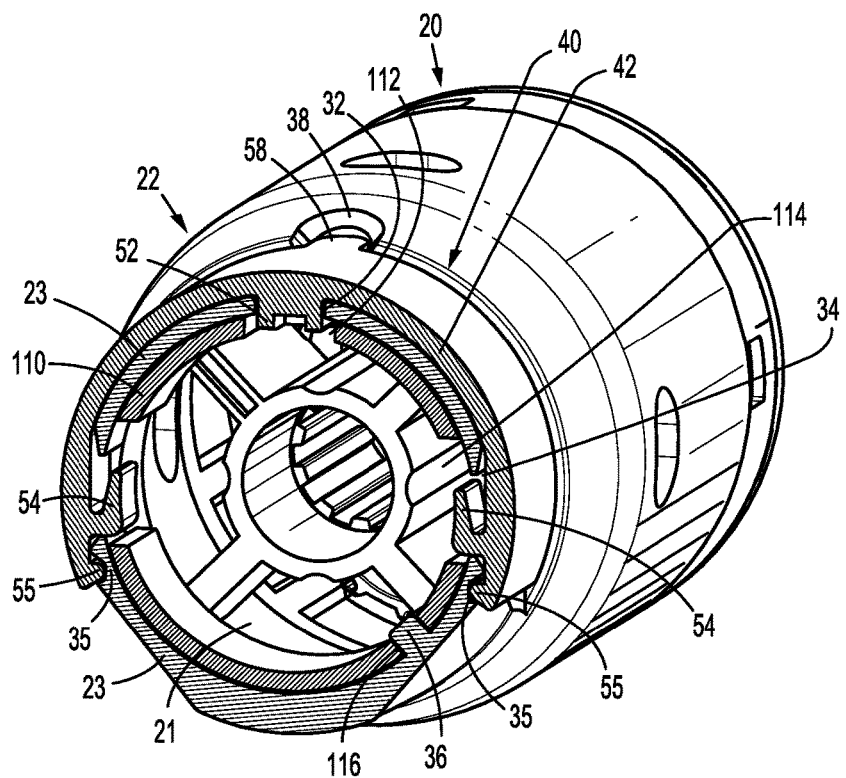
FIG. 13 is a cross-sectional view taken along the section line 13-13 of FIG. 12.
Figure 14:
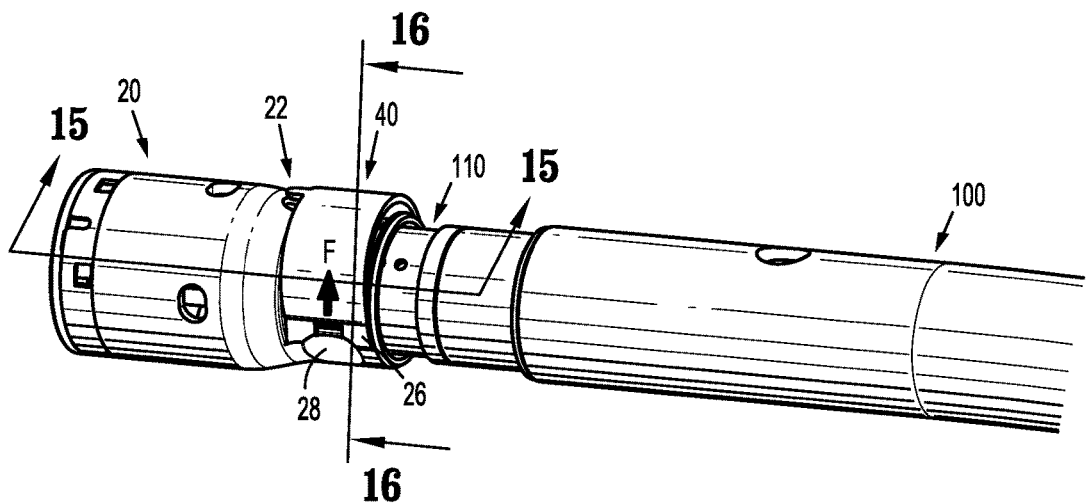
FIG. 14 is a side view of the distal end portion of the adapter and loading unit shown in FIG. 9 with the locking band of the loading unit in a released configuration.
Figure 15:
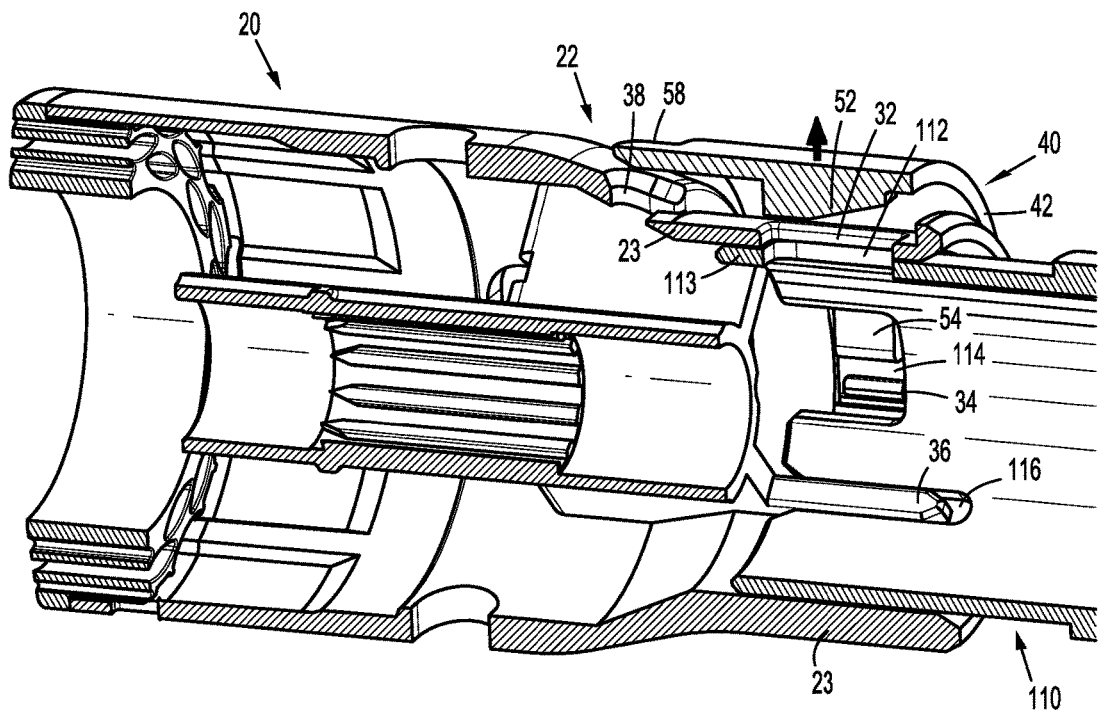
FIG. 15 is a cross-sectional view taken along the section line 15-15 of FIG. 14.

With reference to FIGS. 12 and 13, additional insertion of the distal end portion 110 of the adapter 100 into the central passage 21 of the annular body 23 slides the lift section 113 past the vertical surface 53b of the lug 52 such that the lug window 112 moves into alignment with the lug opening 32. When this occurs, resilience of the body 42 of the locking band 40 snaps or urges the lug 52 into the lug window 112 of the distal end portion 110 of the adapter 100 such that the locking band 40 returns to the locked configuration. When the lug 52 is positioned within the lug window 112, the vertical surface 53b of the lug 52 (FIG. 8) engages the lift section 113 to secure the distal end portion 110 of the adapter 100 within the proximal end 22 of the shell assembly 20 (i.e., the vertical surface 53b prevents the distal end portion 110 of the adapter 100 from withdrawing from the central passage 21 of the proximal end 22 of the shell assembly 20). The key 36 may abut an end of the keyway 116 to prevent the distal end portion 110 of the adapter 100 from over extending into the shell assembly 20. Additionally or alternatively, the retention hooks 54 may engage a proximal wall defining the hook windows 114 to prevent the distal end portion 110 from over extending into the shell assembly 20. With particular reference to FIG. 13, when the lug 52 is positioned within the lug window 112 to secure the shell assembly 20 to the adapter 100, the detents 55 are received within the detent wells 35 and the retention hooks 54 are positioned within the hook windows 114.

When the shell assembly 20 is coupled to the surgical instrument, e.g., the adapter 100, the surgical instrument and shell assembly 20 may be used to perform a surgical procedure. After surgical procedure is completed, the shell assembly 20 can be decoupled or detached from the surgical instrument as will be discussed in detail below. With the shell assembly 20 decoupled from the surgical instrument, another shell assembly may be coupled to the surgical instrument to perform another stapling operation in the surgical procedure. Alternatively, the surgical instrument may be sterilized for use in another surgical procedure, or the surgical instrument may be discarded. In addition, the used shell assembly 20 may be sterilized for use in another surgical procedure or may be discarded.

Figure 16:
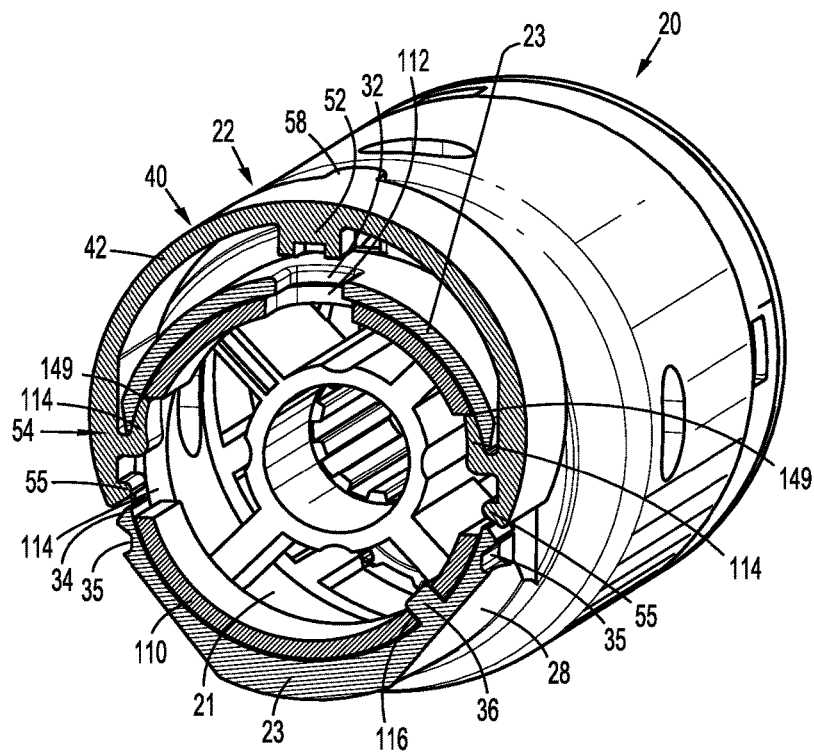
FIG. 16 is a cross-sectional view taken along the section line 16-16 of FIG. 14.

Referring to FIGS. 14-17, the locking band 40 is manipulated to decouple or release the shell assembly 20 from the distal end portion 110 of the adapter 100 such that the shell assembly 20 is removable from the distal end portion 110 of the adapter 100. To release the shell assembly 20, the ends 44 of the locking band 40 are moved or slid towards the lug 52 to transition the locking band 40 to a released configuration as shown by arrow F in FIG. 14. The flats 26 provide access to the ends 44 of the locking band 40 such that the ends 44 are engagable by fingers of a clinician. As shown in FIG. 16, when the ends 44 of the locking band 40 are moved towards the lug 52, the detents 55 are moved out of the detent wells 35. As the detents 55 are lifted from the detent wells 35, the retention hooks 54 hook or engage a portion of the annular body 23 of the shell assembly 20 to prevent the locking band 40 from separating from the shell assembly 20. Specifically, the hook members 144 of the retention hooks 54 engage a portion of the annular body 23 between the hook openings 34 and the lug opening 32. The leading ends 149 of the hook members 144 may engage a wall defining the hook window 114 of the distal end portion 110 and the annular body 23 may engage the support member 142 to prevent excessive movement of the end 44 of the locking band 40 towards the lug opening 32. As the ends 44 are moved towards the lug 52, the body 42 of the locking band 40 flexes to move the lug 52 outward such that the lug 52 is moved outside of the lug window 112 of the adapter 100 and may be moved outside of the lug opening 32 in the annular body 23.

Figure 17:
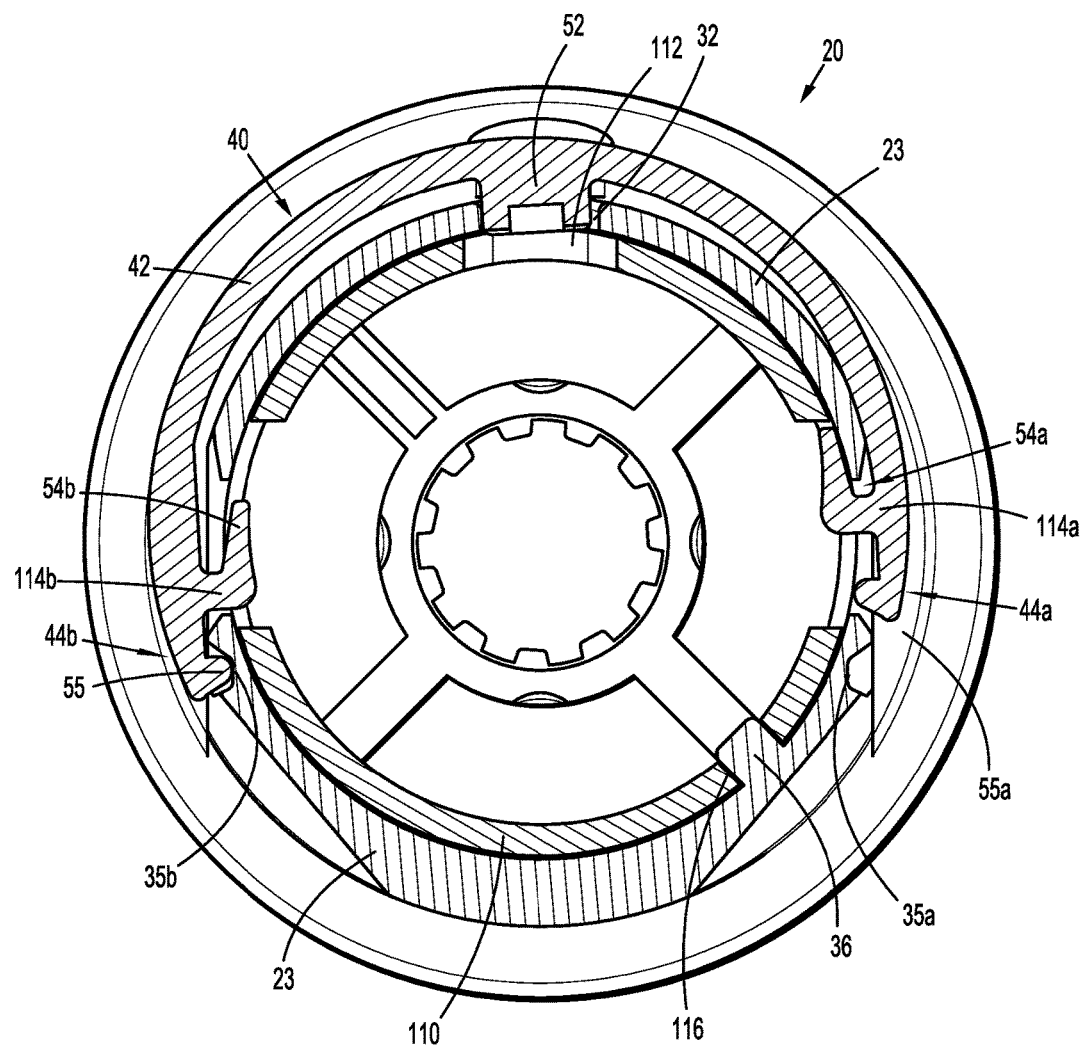
FIG. 17 is a cross-sectional view of the distal end portion of the adapter and loading unit shown in FIG. 14 with the locking band of the loading unit in a released configuration.

With reference to FIG. 17, the locking band 40 may be manipulated to release the shell assembly 20 from the distal end portion 110 of the adapter 100 by engaging one end 44 of the locking band 40. As shown in FIG. 17, when a first end 44a of the locking band 40 is moved towards the lug 52, a first detent 55a adjacent the first end 44a is disengaged from a first detent well 35a and a second detent 55b adjacent a second end 44b remains engaged with a second detent well 35b. As this occurs, the body 42 of the locking band 40 flexes such that the lug 52 is moved outside of the lug window 112 of the adapter 100 such that the adapter 100 is separable from the shell assembly 20. A first retention hook 54a adjacent the first end 44a engages the annular body 23 and/or the distal end portion 110 to prevent excessive movement of the first end 44a towards the lug 52 in a manner similar to that detailed above. A second retention hook 54b adjacent the second end 44b and the second detent 55b engage features of the annular body 23 to resist or prevent movement of the second end 44b as the first end 44a is moved towards the lug 52. Specifically, a support member 114b of the second retention hook 54b engages a wall defining the hook opening 34 in the annular body 23 and the second detent 55b engages the detent well 35b to resist or prevent movement of the second end 44b of the body 42 away from the lug 52.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. The present disclosure is not limited to circular stapling loading units, but has application to loading units for linear stapling or other types of instruments, such as electrocautery or ultrasonic instruments. Therefore, the above description should not be construed as limiting, but merely as exemplifications of particular embodiments. Those skilled in the art will envision other modifications within the scope of the claims appended hereto.

What is claimed:

1. A loading unit comprising:
an annular staple cartridge;
a shell assembly having a proximally extending annular body, the annular body defining two hook openings that oppose one another, a lug opening positioned between the hook openings, and a central passage for receiving a portion of a surgical instrument; and
a locking band having an arced body with two ends, a retention hook positioned adjacent each end of the body and extending from an inner surface of the body, and a lug positioned between the retention hooks and extending from the inner surface of the body, each retention hook extending through a respective one of the hook openings to retain a respective one of the ends of the locking band to the annular body, the lug disposable through the lug opening into the central passage to secure the shell assembly to the surgical instrument.

2. A loading unit comprising:
a shell assembly having a proximally extending annular body, the annular body defining two hook openings that oppose one another, a lug opening positioned between the hook openings, and a central passage for receiving a portion of a surgical instrument; and
a locking band having an arced body with two ends, a retention hook positioned adjacent each end of the body and extending from an inner surface of the body, and a lug positioned between the retention hooks and extending from the inner surface of the body, each retention hook disposed within a respective one of the hook openings to retain a respective one of the ends of the locking band to the annular body, the lug disposable through the lug opening into the central passage to secure the loading unit to the surgical instrument;
wherein each of the retention hooks has a disengaged configuration, and wherein when both of the retention hooks are in the disengaged configuration the lug extends through the lug opening into the central passage.

3. The loading unit according to claim 2, wherein each end of the arced body is moveable to move a respective one of the retention hooks towards an engaged configuration such that a portion of the retention hook engages the annular body between the respective hook opening and the lug window, and wherein movement of the retention hooks towards the engaged position causes the lug to be lifted outside of the central passage of the annular body to release the portion of the surgical instrument from the locking band.

4. The loading unit according to claim 1, wherein the annular body defines a recess between the hook openings, the recess being configured to receive the arced body of the locking band.

5. The loading unit according to claim 4, wherein the locking band includes a tab extending distally from the arced body, and wherein the shell assembly defines a tab receiver in communication with the recess, the tab receiver configured to receive the tab of the locking band to radially align the locking band to the shell assembly.

6. The loading unit according to claim 5, wherein the tab is axially aligned with the lug.

7. A loading unit comprising:
an annular staple cartridge;
a shell assembly having a proximally extending annular body, the annular body defining two hook openings that oppose one another, a lug opening positioned between the hook openings, and a central passage for receiving a portion of a surgical instrument; and
a locking band having an arced body with two ends, a retention hook positioned adjacent each end of the body and extending from an inner surface of the body, and a lug positioned between the retention hooks and extending from the inner surface of the body, each retention hook disposed-within a respective one of the hook openings to retain a respective one of the ends of the locking band to the annular body, the lug disposable through the lug opening into the central passage to secure the shell assembly to the surgical instrument;
wherein the annular body includes flats adjacent each hook opening, the flats defining planes that are parallel to one another.

8. The loading unit according to claim 7, wherein each end of the locking band has a linear inner surface that slidably engages a respective one of the flats of the annular body, each retention hook extending inward from a respective one of the linear inner surfaces.

9. The loading unit according to claim 8, wherein each end of the locking band includes a detent extending inwardly from the respective linear inner surface positioned away from the retention hook and the lug, and wherein each of the flats of the annular body defines a detent well configured to receive a respective one of the detents.

10. The loading unit according to claim 9, wherein in a locked configuration of the locking band, each detent of the locking band is received within a respective one of the detent wells and the lug is positioned through the lug opening into the central passage, and wherein in an unlocked configuration of the locking band each detent of the locking band is received within a respective one of the detent wells and the lug is positioned outside of the central passage.

11. The loading unit according to claim 10, wherein in a released configuration of the locking band at least one of the detents is disposed within a respective one of the hook openings and the lug is positioned outside of the central passage.

12. A loading unit comprising:
a shell assembly having a proximally extending annular body, the annular body defining two detent wells defined in an outer surface of the annular body spaced from one another, a lug opening extending through the annular body, and a central passage for receiving a distal end portion of a surgical instrument; and
a locking band having an arced body with two ends, each end having a detent extending from an inner surface of the body, the body including an inwardly extending lug positioned between the ends, the locking band having a locked configuration in which each detent is received within a respective detent well and the lug extends through the lug opening and into the central passage, an unlocked configuration in which each detent is received within a respective detent well and the lug is positioned outside of the central passage, and a released configuration in which at least one detent is positioned about the annular body between a respective detent well and the lug opening and the lug is positioned outside of the central passage;
wherein the annular body defines two flats that are parallel to one another on opposite sides of the annular body, a respective one of the detent wells being defined in each of the flats.

13. The loading unit according to claim 12, wherein the shell assembly defines a hook opening between each of the detent wells and the lug openings.

14. The loading unit according to claim 13, wherein the locking band includes an inwardly extending retention hook positioned between each of the detents and the lug, the retention hooks being configured to engage the annular body in the released configuration to secure a respective one of the ends of the locking band to the annular body.

15. The loading unit according to claim 13, wherein in the released configuration the at least one detent is positioned in a respective one of the hook openings.

16. The loading unit according to claim 15, wherein the annular body defines two flats that are parallel to one another on opposite sides of the annular body, a respective one of the detent wells and a respective one of the hook openings defined in each of the flats.

17. A surgical system comprising:
a surgical instrument having a distal end portion, the distal end portion defining a lug window;
a loading unit including an annular staple cartridge and a shell assembly supporting the annular staple cartridge, the shell assembly having a proximally extending annular body, the annular body defining two hook openings that oppose one another, a lug opening positioned between the hook openings, and a central passage that receives the distal end portion of the surgical instrument; and
a locking band having an arced body with two ends, a retention hook positioned adjacent each end of the body and extending from an inner surface of the body, and a lug positioned between the retention hooks and extending from the inner surface of the body, each retention hook extending through a respective one of the hook openings to retain a respective one of the ends of the locking band to the annular body, in a locked configuration of the body the lug is disposed through the lug opening of the annular body and the lug window of the surgical instrument to secure the loading unit to the distal end portion of the surgical instrument.

18. The surgical system according to claim 17, wherein the annular body includes a key extending from an inner surface and parallel to a longitudinal axis of the shell assembly, and wherein the distal end portion of the surgical instrument defines a keyway that is parallel to a longitudinal axis of the distal end portion, the keyway slidably receiving the key to rotatably align and fix the shell assembly to the distal end portion of the surgical instrument.

19. The surgical system according to claim 17, wherein the distal end portion defines hook windows that oppose one another, each of the hook windows receiving one of the retention hooks of the locking band.

* * * * *